US006960653B2

(12) United States Patent
McConnell et al.

(10) Patent No.: US 6,960,653 B2
(45) Date of Patent: Nov. 1, 2005

(54) METHOD AND KIT FOR DETECTING, OR DETERMINING THE QUANTITY OF, BETA-LACTAM PENICILLINS

(75) Inventors: Robert Ivan McConnell, Ballymena (GB); Elouard Benchikh, Antrim (GB); Stephen Peter Fitzgerald, Crumlin (GB); John Victor Lamont, Crumlin (GB)

(73) Assignee: Randox Laboratories Limited, Antrim (GB)

( * ) Notice: Subject to any disclaimer, the term of this patent is extended or adjusted under 35 U.S.C. 154(b) by 392 days.

(21) Appl. No.: 10/211,411

(22) Filed: Jul. 31, 2002

(65) Prior Publication Data

US 2003/0143653 A1 Jul. 31, 2003

(30) Foreign Application Priority Data

Aug. 2, 2001 (EP) ............................................ 01202941

(51) Int. Cl.$^7$ ...................... C07K 16/00; G01N 33/532; C07D 499/44

(52) U.S. Cl. ................................ 530/388.9; 530/389.8; 530/404; 435/7.93; 435/188; 436/544; 436/545; 436/546; 436/532; 540/312

(58) Field of Search ........................... 530/388.9, 389.8, 530/404; 435/7.93, 188, 544–546, 532; 540/312

(56) References Cited

U.S. PATENT DOCUMENTS

| | | | |
|---|---|---|---|
| 4,347,312 A | 8/1982 | Brown et al. .................. | 435/7 |
| 4,596,768 A | 6/1986 | Singh et al. ................... | 435/7 |
| 5,128,240 A | 7/1992 | Shah .......................... | 435/7.1 |

FOREIGN PATENT DOCUMENTS

| | | |
|---|---|---|
| DE | 40 13 004 A1 | 10/1991 |
| EP | 0 309 299 A1 | 3/1989 |

OTHER PUBLICATIONS

Cliquet, P. et al., “Generation of class–selective monoclonal antibodies against the penicillin group”, J. Agric. Food Chem. 2001, 49, 3349–3355.* de Haan, P. et al., “Three Epitope–Specific Monoclonal Antibodies against the Hapten Penicillin”, *Int. Archs appl. Immun.*, 1985, 76, 42–46.

De Leuw, P. et al., “Induction and Characterization of Multianalyte Antibodies Against Penicillins in Egg Yolk”, *Journal of AOAC International*, 1997, 80(6), 1220–1228.

Nagakura, N. et al., “Anti–ampicillin monoclonal antibodies and their cross–reactivities to various β–lactams”, *Journal of Antimicrobial Chemotheraphy*, 1991, 28, 357–368.

Shirazi, M.F. et al., “Polyclonal Antibodies Reactive to Some Beta–Lactam Antibiotics”, *The Australian Journal of Diary Technology*, 1991, 88–90.

Useleber, E. et al., “Enzyme Immunoassay for the Detection of Isoxazolyl Penicillin Antibiotics in Milk”, *Analyst*, 1994, 119, 2765–2768.

* cited by examiner

*Primary Examiner*—Mary E. Ceperley
*Assistant Examiner*—Shafiqul Haq
(74) *Attorney, Agent, or Firm*—Woodcock Washburn LLP

(57) ABSTRACT

The invention provides a hapten comprising a 6-[D-α-aminoacetamido] penicillin derivative crosslinked at the α-amino group with a substituted or unsubstituted phenyldicarbaldehyde. In addition, the invention provides an immunogen comprising the aforementioned hapten coupled to an antigenicity-conferring carrier material, a conjugate comprising the aforementioned hapten coupled to a labelling agent, as well as, antibodies raised against the aforementioned immunogen and capable of binding with at least one structural epitope of an intact β-lactam ring.

28 Claims, 3 Drawing Sheets

Reaction Scheme 1

Ampicillin

METHOD AND KIT FOR DETECTING, OR DETERMINING THE QUANTITY OF, BETA-LACTAM PENICILLINS

BACKGROUND TO THE INVENTION

The present invention relates to a method and kit for detecting, or determining the quantity of, β-lactam penicillins, as well as, haptens, immunogens, conjugates and antibodies useful therein.

By "detecting" is meant qualitatively analysing for the presence or absence of a substance.

By "determining" is meant quantitatively analysing for the amount of a substance.

The present invention is intended to have broad applicability across the main first generation β-lactam penicillins such as ampicillin, penicillin G, amoxycillin, cloxacillin, dicloxacillin and oxacillin, but is not intended to be limited to these specific β-lactam penicillins.

Antibiotics are routinely used in animal husbandry for both prophylactic and therapeutic purposes. The β-lactam class of antibiotics are commonly used in the meat and dairy industry, as growth enhancers. This class, also known as the penicillins, is used to treat dairy cow mastitis, thereby increasing milk yields and the productive life span of the cow. β-lactams may also be included in animal feed, with the purpose of enhancing the growth of poultry and pigs. Through disease prevention, or by inhibiting the activity of natural gut flora in such animals, the antibiotic causes the animals to reach marketable size faster than without the use of such enhancers.

Problems, however, may arise when residues of the β-lactams are present in meat and dairy products. As with any antibiotic, continuous exposure of humans to the β-lactams can result in a reduction of the efficiency of the drugs used to treat diseases, due to the development of resistant strains of pathogenic bacteria. The presence of the β-lactams in consumed food may also result in allergic reactions in penicillin sensitive humans. Dairy products containing these antibiotics may also interfere with bacterial cultures used in processing.

As a result, strict guidelines have been imposed throughout the European Community regarding withdrawal times and the maximum recommended levels (MRLs) of the β-lactams in milk and meat. Milk and meat samples are routinely tested to ensure that they comply with this EC legislation. Various methods are used to test for antibiotics such as the β-lactams. Many of these tests are based on microbial inhibition tests, which are time consuming and may be specific for individual β-lactams. The development of a method for the rapid detection of the β-lactams in milk and meat would be especially valuable if the method was generic, i.e., detected most, if not all, β-lactam antibiotics.

Many attempts have been made to raise antibodies in β-lactam sensitised animals, with the aim of producing an immunoassay for the detection of β-lactams in general. The first stage of such a process is to produce an immunogen which will elicit an immune response in the animal host. This is problematic due to the failure of the β-lactam ring to remain intact during conjugation to a carrier protein. Known conjugation methods based on the open lactam ring are disclosed in, for example, U.S. Pat. No. 4,347,312, U.S. Pat. No. 5,128,240, in de Haan et al, 1985 and in Faghihi Shirazi et al, 1991. This results in the production of antisera sensitive to the open form of the β-lactam ring, which may not necessarily be sensitive to the generic ring structure.

Alternatively, for example, the free carboxyl group of the closed β-lactam ring may be esterified, as is disclosed in EP-A-309,299 and in Usleber et al, 1994. Antisera raised to β-lactam antibiotics conjugated in this manner are specific for the acyl side chains and only cross react with other β-lactam antibiotics if they have similar side chains, as is the case with the isoxazolyl penicillins. Further, alternatively, conjugation can occur by way of the 6-amino group of 6-amino penicillanic acid, as is disclosed in EP-A-309,299 and de Leuw et al, 1997. In such cases, where the β-lactam ring remains intact during conjugation, the antibodies display high cross reactivity with the main first generation β-lactams. A further potential conjugation site for β-lactam penicillins is via the a amino group of the D-α-aminoacetamido group of penicillin, as is disclosed in, for example, Nagakura et al, 1991. The cell lines disclosed in Nagakura et al, 1991, Abp4 and Abp7, concern haptens and conjugates using a MBS (maleimidobenzoyl-N-hydroxysuccinimide) cross-linker and the document concludes that one of the cell lines (Abp4) recognises the thiazolidine ring whilst the other of the cell lines (Abp7) recognises the acyl side chain. Abp4 cross reacts with penicillin G, 6-aminopenicillanic acid and certain cephalosporins, while Abp7 is highly specific, displaying little or no cross reactivity with the main first generation β-lactams.

BIBLIOGRAPHY

Faghihi Shirazi M., Hung T V., Womersley D M. 1991. Polyclonal antibodies reactive to some Beta-Lactam antibiotics. Australian Journal of Dairy Technology, 46(2), 88–90.

De Haan P., de Jonge A. J. R, Verbrugge T. and Boorsma D. M., 1985. Three epitope specific monoclonal antibodies against the hapten penicillin. Int. Arch. Allergy Appl Immun. 76: 42–46.

De Leuw P., Kapa G. and Petz M., 1997. Production and Characterisation of Multianalyte Antibodies against penicillins in egg yolk. J. of AOAC International 80(6): 1220–8.

Nagakura N., Souma S., Shimizu T., Yanagihara Y., 1991. Anti-ampicillin monoclonal antibodies and their cross-reactivities to various β-lactams. J. of Antimicrobial Chemotherapy 28: 357–368.

Usleber, E., Lorber, M. Straka M., Terplan G., Martlbauer E., 1994. Enzyme Immunoassay for the Detection of Isoxazolyl Penicillin Antibiotics in Milk. Analyst, 119, 2765–2768.

SUMMARY OF THE INVENTION

The present invention describes the conjugation of a novel hapten (ampicillin derivative) at the α amino group of the D-α-aminoacetamido group of penicillin to an antigenicity-conferring carrier material to produce an immunogen. It also describes how antibodies generated to this immunogen are employed in the development of a generic assay which can be used to test milk and meat and the like for the presence of β-lactam antibiotics.

The invention provides a hapten comprising a 6-[D-α-aminoacetamido]penicillin derivative crosslinked at the -α-amino group with a substituted or unsubstituted phenyldicarbaldehyde. In addition, the invention provides an immunogen comprising the aforementioned hapten coupled to an antigenicity-conferring carrier material, a conjugate comprising the aforementioned hapten coupled to a labelling agent, as well as, antibodies raised against the aforementioned immunogen and capable of binding with at least one structural epitope of an intact β-lactam ring.

The invention further provides a method and a kit for detecting, or determining the quantity of, β-lactam antibiotics, as well as, use of the aforementioned conjugate with the aforementioned antibodies for detecting, or determining the quantity of, β-lactam antibiotics.

The present invention has broad specificity across the main first generation β-lactams and can be used to test milk and meat and the like for the presence of residual β-lactani antibiotics.

DETAILED DESCRIPTION OF INVENTION

In a first aspect, the invention provides a hapten comprising a 6-[D-α-aminoacetamido] penicillin derivative crosslinked at the α-amino group with a substituted or unsubstituted phenyldicarbaldehyde selected from the group consisting of substituted or unsubstituted phthalaldehyde, substituted or unsubstituted isophthalaldehyde and substituted or unsubstituted terephthalaldehyde.

A representative 6-[D-α-aminoacetamido]penicillin derivative has the structural formula:

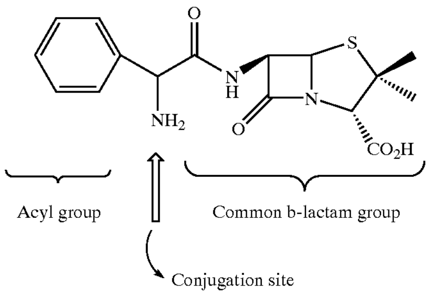

and the conjugation site is identified by an arrow.

Preferably, the phenyldicarbaldehyde is a substituted or unsubstituted terephthalaldehyde, most preferably unsubstituted terephthalaldehyde. Suitable substitutions include the addition of aldehyde, thioisocyanate and N-hydroxysuccinimide functional groups at the para- and ortho- positions.

The haptens are prepared by reacting a substituted or unsubstituted phenyldicarbaldehyde with a 6-[D-α-aminoacetamido]penicillin derivative in a suitable solvent, of which dimethylformamide and dimethylsulfoxide are suitable examples.

In a further aspect, the present invention concerns an immunogen comprising the hapten of the present invention coupled to an antigenicity-conferring carrier material. Preferably, the carrier material is a protein, a protein fragment, a synthetic polypeptide or a semi-synthetic polypeptide.

In a still further aspect, the present invention concerns antibodies raised against the immunogen of the present invention, the antibodies being capable of binding with at least one structural epitope of an intact β-lactam ring. Preferably, the antibodies are fixed on a backing substrate.

The invention further provides a process of preparing the antibodies, the process comprising the steps of immunising an animal, preferably a vertebrate animal, most preferably a mammalian animal by repeated administration of an immunogen of the present invention; and collecting the resulting serum antibodies from the immunised animal. Preferably, the process further comprises fixing said serum antibodies to a backing substrate, preferably a solid support, most preferably a polystyrene solid support. Preferably the antibodies are polyclonal. Alternatively the antibodies are monoclonal.

In a still further aspect, the present invention comprises a conjugate comprising the hapten of the present invention covalently bonded to a detectable labelling agent. Preferably, the labelling agent is selected from an enzyme, a luminescent substance, a radioactive substance, or a mixture thereof. Preferably, the labelling agent is an enzyme, preferably a peroxidase, most preferably horseradish peroxidase (HRP). Alternatively or additionally, the luminescent substance may be a bioluminescent, chemiluminescent or fluorescent material.

In a still further aspect, the present invention comprises a method for detecting, or determining the quantity of, β-lactam penicillins in a sample, the method comprising contacting the sample with the conjugate of the present invention, or a mixture thereof, and with antibodies of the present invention, or a mixture thereof; detecting or determining the quantity of bound conjugate; and deducing from a calibration curve the presence or amount of β-lactam penicillins in the sample.

Preferably the antibodies are polyclonal.

In a further aspect, the, invention includes a kit for detecting, or determining the quantity of, β-lactam penicillins, the kit including the conjugate of the present invention, or a mixture thereof, and the antibodies of the present invention, or a mixture thereof. The kit may optionally include instructions for the use of said conjugate(s) and said antibodies for detecting, or determining the quantity of, β-lactam penicillins in a sample.

Preferably, the sample is a solution, such as a biological fluid, including milk; or a cellular tissue cutting, such as meat.

In the method and kit of the present invention, the respective crosslinkers (of the immunogen and the conjugate), crosslinked at the α-amino position, may be the same or different.

In a further aspect, the present invention involves use of the conjugates according to the present invention, or a mixture thereof, with the antibodies according to the present invention, or a mixture thereof, to test samples such as milk and meat for detecting, or determining the quantity of, β-lactam antibiotics.

The present invention relates to novel haptens which are employed in the preparation of novel immunogens by conjugation to conventional antigenicity-conferring carrier materials. The resulting immunogen is then administered to animals, preferably vertebrate hosts, most preferably mammalian hosts, to elicit production of avid polyclonal antisera which are then used to develop a generic immunoassay for the β-lactam penicillins, employing a conjugate (hapten-labelling agent), or a mixture thereof, as the detection reagent.

The chemical structure of ampicillin and the other β-lactam penicillins are summarised in the following table, having regard to the structural formula set out below:

TABLE 1

Chemical structures of the β-lactam penicillins

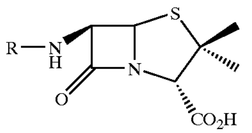

| Penicillin | R |
|---|---|
| Penicillin G | $PhCH_2CO$ |
| Penicillin V | $PhOCH_2CO$ |
| Ampicillin | D-PhCH $(NH_2)CO$ |

TABLE 1-continued

Chemical structures of the β-lactam penicillins

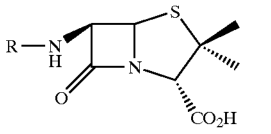

| Penicillin | R |
|---|---|
| Amoxycillin | D-(p-Hydroxy)PhCH($NH_2$)CO |
| Oxacillin | 5-methyl-3-phenyl-4-isoxazolyl-carbonyl |
| Cloxacillin | 5-methyl-3-(O-chlorophenyl)-4-isoxazolyl-carbonyl |
| Dicloxacillin | 5-methyl-3-(O,O'-dichlorophenyl)-4-isoxazolyl-carbonyl |
| 6-Aminopenicillanic Acid | H |

The focus of the present invention is the preparation of antibodies specific for the entire group of β-lactam penicillins. In order to achieve this broad specificity, ampicillin is derivatized through the amino group employing a bifunctional cross linker such as a substituted or unsubstituted phenyldicarbaldehyde, preferably substituted or unsubstituted terephthalaldehyde (unsubstituted terephthalaldehyde is shown in FIG. 1 of the accompanying drawings). The β-lactam ring of ampicillin is conserved during derivatization to ensure that the epitopes common to the penicillin group are retained.

Although the hapten of the present invention (ampicillin derivative) provides defined structural epitopes, it is not in itself immunogenic and therefore must be conjugated to a suitable antigenicity-conferring carrier material, so that the thus-formed immunogen will elicit an immunogenic response when injected into a host animal. Suitable antigenicity-conferring carrier materials include proteins and proteins fragments such as albumins, serum proteins e.g. globulins, ocular lens proteins and lipoproteins. Illustrative protein carriers include bovine serum albumin, egg ovalbumin, bovine gamma globulin, thyroxine binding globulin, keyhole limpet haemocyanin etc. Alternatively, synthetic poly(amino acids) having a sufficient number of available amine groups such as lysine may be employed, as may other synthetic or natural polymeric materials bearing reactive functional groups. In particular, carbohydrates, yeasts or polysaccharides may be conjugated to the hapten to produce an immunogen of the present invention.

The hapten (ampicillin derivative) is also conjugated to a labelling agent such as an enzyme (for example, horseradish peroxidase), a fluorescent substance or a radioactive substance to produce a detection reagent for use in the immunoassay. The fluorescent substance may be, for example, a monovalent residue of fluorescein or a derivative thereof.

Preparation of the hapten and its conjugation either to the carrier material or to the labelling agent (e.g. enzyme or other label) is performed according to Reaction Scheme 1 set out in FIG. 1. Thus, for example, ampicillin is reacted with terephthalaldehyde in dimethylformamide at room temperature for 18 hours to produce a Schiff base intermediate. The intermediate is reacted with either the carrier material (for example, bovine serum albumin) or with the labelling agent (e.g., enzyme or label) in acetate buffer at pH4–5 and this is followed by reduction of the Schiff base with, for example, sodium cyanoborohydride to yield either the immunogen of the present invention or the conjugate of the present invention, respectively.

In order to confirm that adequate conjugation of hapten to carrier material has been achieved, prior to, immunisation, each immunogen is evaluated using matrix-assisted UV laser desorption/ionization mass spectrometry (MALDI MS). In the case of the preferred carrier material, bovine serum albumin, a minimum of 6 molecules of hapten per carrier molecule is preferred.

In order to generate polyclonal antisera, the immunogen is mixed with Freund's Adjuvant and the mixture is injected into a host animal, such as a rabbit, sheep, mouse, guinea pig or horse. Further injections (boosts) are made and serum is sampled for evaluation of antibody titer. When the optimal titer has been reached, the host animal is then bled to yield a suitable volume of specific antiserum. The degree of antibody purification required depends on the intended application. For many purposes, there is no requirement at all for purification, however, in other cases, such as where the antibody is to be immobilised on a solid support, purification steps can be taken to remove undesired material and reduce or eliminate non-specific binding.

The antibodies generated to ampicillin are useful as reagents in biochemical assays for the determination of the presence of β-lactam penicillins in biological fluids such as milk and in food products such as meat.

IN THE DRAWINGS

FIG. 1 concerns Reaction Scheme 1, which is a general reaction scheme for the preparation of a hapten according to the present invention and its subsequent conjugation to either a carrier material or a labelling agent, to form an immunogen according to the present invention or a conjugate according to the present invention;

FIG. 2 schematically illustrates a competitive ELISA titration assay on a microtiter plate;

EXAMPLE 1

Figure 1:
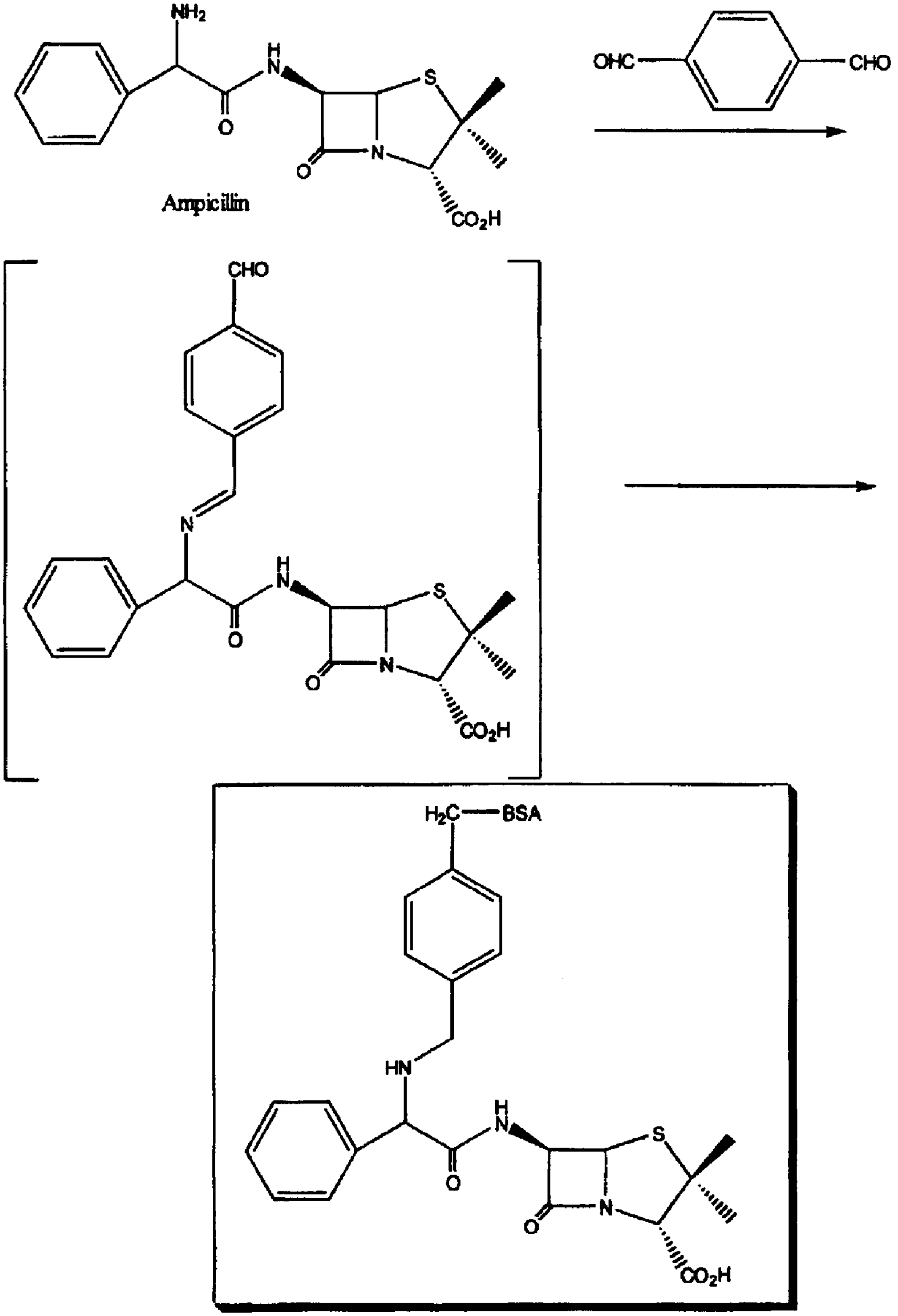

Preparation of Hapten 183 mg (1.364 mmole) of terephthalaldehyde was added under nitrogen to a solution of 500 mg (1.24 mmole) of ampicillin trihydrate in 10 ml dimethylformamide at 20° C. The mixture was protected from light and stirred for 24 hours at room temperature. To confirm the reaction was complete, thin layer chromatography (TLC) (80% chloroform, 20% methanol v/v) was performed which showed no remaining starting materials and the formation of a new spot less polar than ampicillin. The hapten solution was stored under nitrogen at −20° C. (stable for 1 year).

EXAMPLE 2

Preparation of Immunogen (Hapten-Bovine Serum Albumin)

The hapten solution prepared in Example 1 was added dropwise to a solution of 200 mg of bovine serum albumin (BSA) in 10 ml of 0.1M sodium acetate buffer, pH 4.1. The mixture was protected from light and stirred at room temperature for 4 hours. Reduction of the Schiff base was accomplished by addition of 30 mg of sodium cyanoborohydride. The mixture was stirred for 90 mins and 5 mg sodium borohydride was added. After stirring for a further 10 mins, the mixture was dialysed against phosphate buffered saline, pH 7.2, at 4° C. for 24 hours (3 changes). The extent of conjugation of hapten to BSA was evaluated by MALDI MS, which revealed a conjugation ratio of 6.3 hapten molecules to one molecule of BSA.

EXAMPLE 3

Preparation of Conjugate (Hapten-HRP)

The conjugation of the hapten of Example 1 to HRP was performed in a similar manner to that described for the preparation of the immunogen. 40 μl of the hapten solution prepared in Example 1 was added to 20 mg HRP (horseradish peroxidase) in 2 ml of 0.1M sodium acetate buffer at pH4–5. The mixture was protected from light and stirred for 4 hours at room temperature. Sodium cyanoborohydride (0.7 mg) was added and the mixture was stirred for 90 mins. The conjugate was purified using two PD-10 columns (Pharmacia Biotech) and dialysed overnight, protected from light, against double deionised water at 2–8° C.

EXAMPLE 4

Preparation of Antibodies Raised Against the Immunogen of Example 2

An aqueous solution of the immunogen of Example 2 was formulated with Freund's Complete Adjuvant (FCA) to form an emulsion consisting of 2 mg/ml immunogen in 50% (v/v) FCA. Three sheep were immunised with this emulsion, 0.25 ml being subcutaneously injected at each of 4 sites in the flank of each animal. Subsequent immunisations (boosts) contained 1 mg/ml immunogen emulsified in 50% (v/v) Freund's Incomplete Adjuvant (FIA) and were administered in the same manner at monthly intervals for 1 year. Blood sampling took place 7 to 14 days after each boost. Each sample was processed to produce antiserum which was further purified by caprylic acid and ammonium sulfate precipitation to yield an immunoglobulin G (IgG) fraction. The IgG fraction was evaluated by competitive ELISA, microtiter plate assay, as described below.

EXAMPLE 5

Development of a Competitive ELISA

Figure 2:
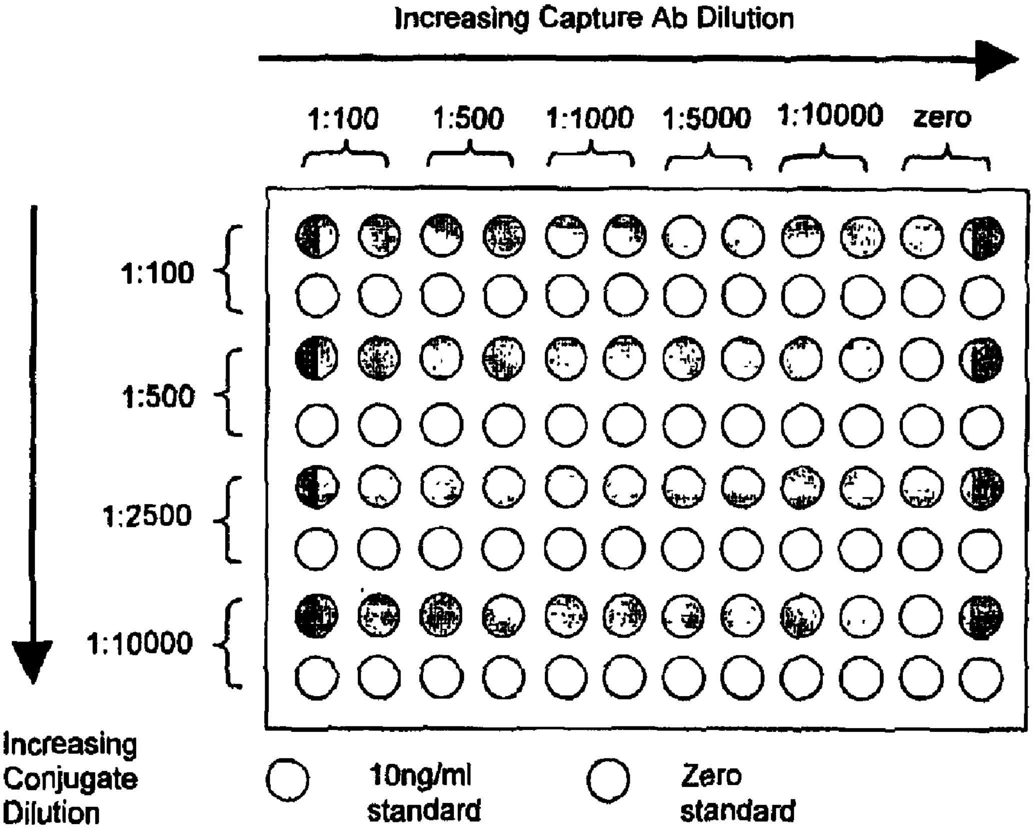

A checkerboard titration was performed to determine optimum capture antibody and conjugate (ampicillin-HRP) concentrations. Serial dilutions of the IgG fraction of each antiserum to be tested (prepared in accordance with Example 4) were prepared in 10 mM Tris, pH 8.5. The wells of an enhanced binding 96 well polystyrene microtiter plate were coated with these dilutions (as shown in FIG. 2) by incubation at 37° C. for 2 hours (125 μl/well). The plate was washed 4 times with Tris buffered saline (pH7.4) containing Tween (Trade Mark) 20 (TBST) and tapped dry. 50 μl of a 10 ng/ml solution of ampicillin (mid assay range) in TBST was added to the appropriate wells (FIG. 2). 50 μl of TBST was added to the remaining (control) wells. Serial dilutions of conjugate (ampicillin-HRP) were prepared in Tris buffer at pH7.2 containing EDTA, D-mannitol, sucrose, thimerosal and BSA and 75 μl of each dilution was added to the wells, as shown in FIG. 2. The plate was incubated at 37° C. for 2 hours. The excess unbound conjugate was removed by washing 6 times over a 10 minute period with TBST. 125 μl of tetramethylbenzidine (TMB) substrate solution was added to each well of the plate, which was then incubated for 15 to 20 minutes, in the dark, at room temperature. The reaction was terminated by addition of 125 μl 0.2M $H_2SO_4$ to each well. The absorbance was then measured at 450 nm using a microtiter plate reader. A 1/1000dilution of capture antibody in combination with a 1/15000dilution of conjugate produced an acceptable top absorbance of 2.15 and a significant drop in absorbance between the 0 and 10 ng/ml antigen concentrations of 80%.

Figure 3:
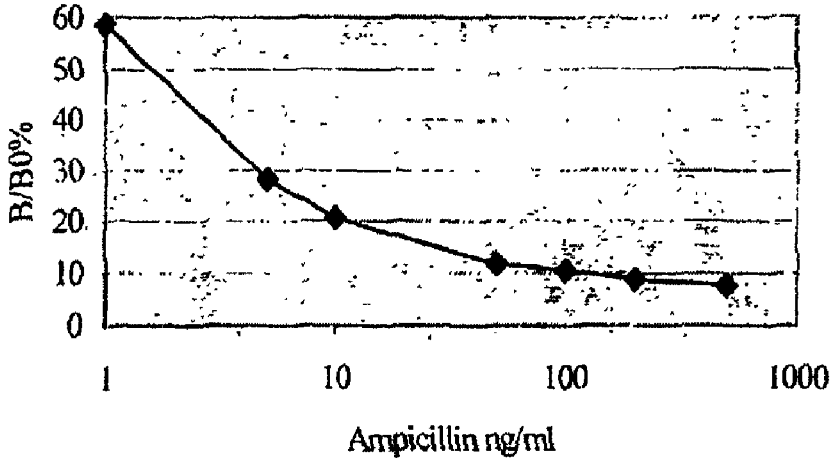
FIG. 3 is a calibration curve for a competitive ELISA.

A microtiter plate was then coated with the IgG fraction of anti-ampicillin antiserum at the optimum coating dilution of 1/1000in Tris, pH8.5, as outlined above. Standard solutions of ampicillin (sodium salt) were prepared in TBST and applied at the following concentrations: 0, 1, 5, 10, 50, 100, 200, 500 ng/ml. The data generated resulted in the sensitive calibration curve illustrated in FIG. 3 where B is the absorbance measured at 450 nm for xng/ml ampicillin and $B_0$ is the absorbance measured at 450 nm for 0 ng/ml ampicillin.

EXAMPLE 6

Figure 4:
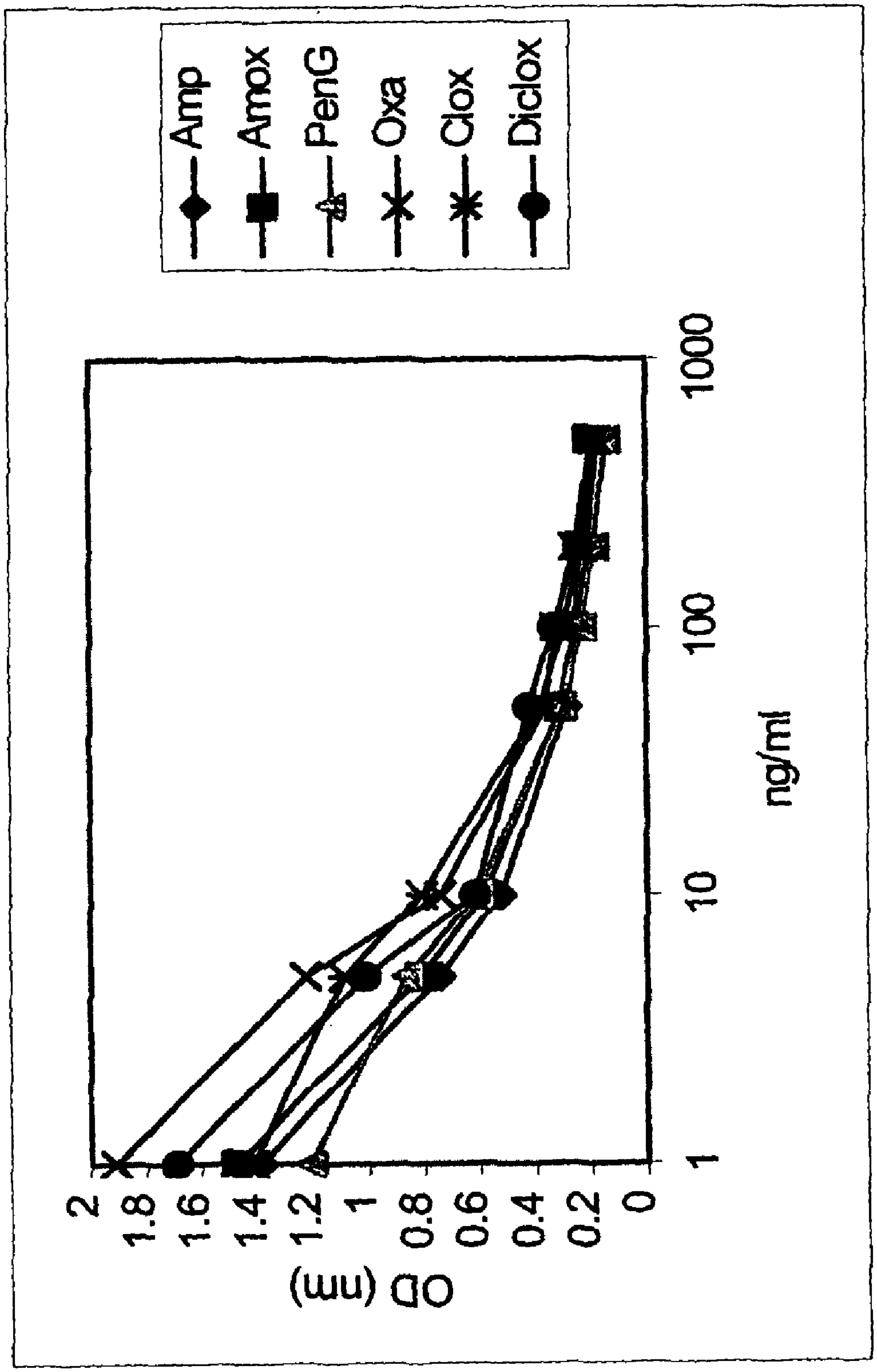
FIG. 4 is a calibration curve generated employing each of the beta lactam penicillins as a standard in an ELISA.

Cross Reactivity of the Ampicillin Immunoassay with Each of the β-lactam Penicillins Standard solutions of benzylpenicillin (penicillin G-PenG), amoxycillin (Amox), cloxacillin (Clox), dicloxacillin (Diclox) and oxacillin (Oxa) were prepared in TBST at 0, 1, 5, 10, 50, 100, 200 and 500 ng/ml. Calibration curves were generated employing each of the β-lactam penicillin standards in the ampicillin immunoassay (FIG. 4) and these were used to determine the cross-reactivity of the immunoassay with each penicillin. The results of this study are presented in Table 2, cross reactivity being calculated according to the following formula:

$$\% CR = IC50_{amp}/IC50_{pen} \times 100$$

where % CR is the percentage cross-reactivity, $IC50_{amp}$ is the concentration of ampicillin which causes 50% displacement of signal and $IC50_{pen}$ is the concentration of β-lactam penicillin, for which % CR is being evaluated, which causes 50% displacement of signal.

The ampicillin immunoassay exhibited a high level of cross-reactivity with each of the β-lactam penicillins (Table 2). By high level of cross-reactivity is meant a cross-reactivity of greater than 35%, relative to 100% for ampicillin. The present immunoassay is most specific for ampicillin (100% CR), amoxycillin (87% CR) and benzylpenicillin (72% CR). Since the maximum recommended levels (MRL) for amoxycillin, ampicillin and benzylpenicillin in milk are each 4 μg/kg and for oxacillin, cloxacillin and dicloxacillin are each 30 μg/kg, the IC50 values determined for each of the β-lactam penicillins suggest that the ELISA described is suitable for use as a generic immunoassay for β-lactam antibiotics in compliance with EC regulations, 2377/90.

TABLE 2

Cross reactivity of the ampicillin immunoassay with the β-lactam penicillins.

| | Assay 1 | | Assay 2 | | Assay 3 | | Mean Results | | |
|---|---|---|---|---|---|---|---|---|---|
| β-Lactam | IC50 ng/ml | % CR | IC50 ng/ml | % CR | IC50 ng/ml | % CR | IC50 ng/ml | % CR | MRLs μg/kg |
| Amp | 1.7 | 100 | 2.5 | 100 | 2.5 | 100 | 2.2 | 100 | 4 |
| Amox | 1.8 | 94 | 3.0 | 83 | 3.0 | 83 | 2.6 | 87 | 4 |

TABLE 2-continued

Cross reactivity of the ampicillin immunoassay with the β-lactam penicillins.

| | Assay 1 | | Assay 2 | | Assay 3 | | Mean Results | | |
|---|---|---|---|---|---|---|---|---|---|
| β-Lactam | IC50 ng/ml | % CR | IC50 ng/ml | % CR | IC50 ng/ml | % CR | IC50 ng/ml | % CR | MRLs μg/kg |
| PenG | 2.7 | 63 | 3.2 | 78 | 3.4 | 74 | 3.1 | 72 | 4 |
| Oxa | 4.0 | 42.5 | 7.0 | 36 | 6.6 | 38 | 5.9 | 39 | 30 |
| Cloxa | 3.4 | 50 | 5.8 | 43 | 5.8 | 43 | 5 | 45 | 30 |
| Dicloxa | 3.8 | 45 | 6.0 | 42 | 4.9 | 51 | 4.9 | 46 | 30 |

EXAMPLE 7

Qualitative Analysis of β-lactam Antibiotics in Milk Employing the Generic Immunoassay.

A range of milk samples were tested for the presence of β-lactam antibiotics using standard antimicrobial methods. These samples with assigned values were then tested using the present ELISA. Microtitre plates were coated and reagents were prepared as described in Example 5. The immunoassay procedure was adapted as follows. A 1% solution of milk buffer at pH7.4 was prepared by dissolving skimmed milk powder in distilled water and 25 μl of this buffer was added to the wells of the plate. Following the addition of the milk buffer, ampicillin standards were loaded (25 μl per well), followed by milk samples (25 μl per well). Both standards and samples were run in duplicate. Conjugate (ampicillin-HRP) was then added (75 μl per well), and the microtitre plate incubated for 2 hours at 37° C. for the competition reaction to take place. After the competition reaction, the plate was washed and developed using the same procedure as described in Example 5. The results of the analysis are shown in Table 3, which shows the calculated concentrations for a range of milk samples tested by the generic β-lactam ELISA described. The β-lactam ELISA described was used to test milk samples known to be negative for the presence of β-lactams (samples 1–6), as well as confirmed β-lactam positive samples (samples 7 & 8).

The ELISA results confirm that samples 1–6 are negative and that samples 7 and 8 are positive for β-lactam antibiotic content (see Table 3).

The results of the ELISA, shown in Table 3, demonstrate that the immunoassay can be used successfully to screen milk samples for the presence of β-lactams. Negative samples tested by ELISA were confirmed as negative, and known positive samples were confirmed as positive.

TABLE 3

| Milk Sample | Absorbance | CV % | Calculated Concn. (ng/ml) |
|---|---|---|---|
| 1 | 1.906 | 2.2 | Neg |
| 2 | 1.826 | 1.7 | Neg |
| 3 | 2.083 | 1.6 | Neg |
| 4 | 1.857 | 0.1 | Neg |
| 5 | 1.754 | 3.1 | Neg |
| 6 | 1.719 | 0.9 | Neg |
| 7 | 0.718 | 9.0 | 126.19 |
| 8 | 0.914 | 7.8 | 66.79 |

What is claimed is:

1. A hapten comprising a 6-[D-α-aminoacetamido] penicillin derivative crosslinked at the α-amino group with a substituted or unsubstituted phenyldicarbaldehyde selected from the group consisting of substituted or unsubstituted phthalaldehyde, substituted or unsubstituted isophthalaldehyde and substituted or unsubstituted terephthalaldehyde.

2. A hapten according to claim 1, wherein the phenyldicarbaldehyde is a substituted or unsubstituted terephthalaldehyde.

3. A process for preparing a hapten, wherein a substituted or unsubstituted phenyldicarbaldehyde selected from the group consisting of substituted or unsubstituted phthalaldehyde, substituted or unsubstituted isophthalaldehyde, and substituted or unsubstituted terephthalaldehyde, or a mixture thereof, is reacted with a 6-[D-α-aminoacetamido] penicillin derivative in a solvent selected from the group consisting of dimethylformamide and dimethylsulfoxide.

4. An immunogen comprising a hapten, wherein said hapten comprises a 6-[D-α-aminoacetamido] penicillin derivative crosslinked at the α amino group with a substituted or unsubstituted phenyldicarbaldehyde selected from the group consisting of substituted or unsubstituted phthalaldehyde, substituted or unsubstituted isophthalaldehyde, and substituted or unsubstituted terephthalaldehyde, or a mixture thereof, coupled, through a terminal aldehyde on the substituted or unsubstituted phenyldicarbaldehyde, to an antigenicity-conferring carrier material.

5. The immunogen of claim 4, wherein the carrier material is a protein, a protein fragment, a synthetic polypeptide or a semi-synthetic polypeptide.

6. Antibodies raised against an immunogen, wherein said immunogen comprises a hapten, wherein said hapten comprises a 6-[D-α-aminoacetamido] penicillin derivative crosslinked at the α-amino group with a substituted or unsubstituted phenyldicarbaldehyde selected from the group consisting of substituted or unsubstituted phthalaldehyde, substituted or unsubstituted isophthalaldehyde, and substituted or unsubstituted terephthalaldehyde, or a mixture thereof, coupled, through a terminal aldehyde on the substituted or unsubstituted phenyldicarbaldehyde, to an antigenicity-conferring carrier material.

7. The antibodies of claim 6, wherein said antibodies are fixed on a backing substrate.

8. A process of preparing antibodies, the process comprising the steps of immunising an animal by repeated administration of an immunogen, wherein said immunogen comprises a hapten, wherein said hapten comprises a 6-[D-α-aminoacetamido] penicillin derivative crosslinked at the α-amino group with a substituted or unsubstituted phenyldicarbaldehyde selected from the group consisting of substituted or unsubstituted phthalaldehyde, substituted or unsubstituted isophthalaldehyde, and substituted or unsubstituted terephthalaldehyde, or a mixture thereof, coupled, through a terminal aldehyde on the substituted or unsubstituted phenyldicarbaldehyde, to an antigenicity-conferring carrier material, and collecting the resulting serum antibodies from the immunised animal.

9. The process of claim 8, wherein the process further comprises fixing said serum antibodies to a backing substrate.

10. A conjugate comprising a hapten, wherein said hapten comprises a 6-[D-α-aminoacetamido] penicillin derivative crosslinked at the α-amino group with a substituted or unsubstituted phenyldicarbaldehyde selected from the group consisting of substituted or unsubstituted phthalaldehyde, substituted or unsubstituted isophthalaldehyde, and substituted or unsubstituted terephthalaldehyde, or a mixture thereof, covalently bonded, through a terminal aldehyde on the substituted or unsubstituted phenyldicarbaldehyde, to a labelling agent which is detectable.

11. The conjugate of claim 10, wherein the labelling agent is an enzyme, a luminescent substance, a radioactive substance, or a mixture thereof.

12. A method for detecting, or determining the quantity of, β-lactam penicillins in a sample, the method comprising contacting the sample with a conjugate according to claim 10, or a mixture thereof, and with antibodies, raised against an immunogen, wherein said immunogen comprises a hapten comprising a 6-[D-α-aminoacetamido] penicillin derivative crosslinked at the α-amino group with a substituted or unsubstituted phenyldicarbaldehyde selected from the group consisting of substituted or unsubstituted phthalaldehyde, substituted or unsubstituted isophthalaldehyde and substituted or unsubstituted terephthalaldehyde, or a mixture thereof, coupled, through a terminal aldehyde on the substituted or unsubstituted phenyldicarbaldehyde, to an antigenicity-conferring carrier material, or a mixture of said antibodies; detecting, or determining the quantity of, bound conjugate; and deducing from a calibration curve the presence, or amount of, β-lactam penicillins in the sample.

13. A kit for detecting, or determining the quantity of, β-lactam penicillins, the kit including a conjugate according to claim 10, or a mixture thereof, and antibodies raised against an immunogen, wherein said immunogen comprises a hapten comprising a 6-[D-α-aminoacetamido] penicillin derivative crosslinked at the α-amino group with a substituted or unsubstituted phenyldicarbaldehyde selected from the group consisting of substituted or unsubstituted phthalaldehyde, substituted or unsubstituted isophthalaldehyde and substituted or unsubstituted terephthalaldehyde, or a mixture thereof, coupled, through a terminal aldehyde on the substituted or unsubstituted phenyldicarbaldehyde, to an antigenicity-conferring carrier material, or a mixture of said antibodies.

14. The hapten of claim 2, wherein the phenyldicarbaldehyde is an unsubstituted terephthalaldehyde.

15. The process of claim 3, wherein the phenyldicarbaldehyde is a substituted or unsubstituted terephthalaldehyde.

16. The process of claim 15, wherein the phenyldicarbaldehyde is an unsubstituted terephthalaldehyde.

17. The immunogen of claim 4, wherein the phenyldicarbaldehyde is a substituted or unsubstituted terephthalaldehyde.

18. The immunogen of claim 17, wherein the phenyldicarbaldehyde is an unsubstituted terephthalaldehyde.

19. The antibodies of claim 6, wherein the phenyldicarbaldehyde is a substituted or unsubstituted terephthalaldehyde.

20. The antibodies of claim 19, wherein the phenyldicarbaldehyde is an unsubstituted terephthalaldehyde.

21. The antibodies of claim 6, wherein said antibodies are capable of binding with at least one structural epitope of an intact β-lactam ring.

22. The process of claim 8, wherein the phenyldicarbaldehyde is a substituted or unsubstituted terephthalaldehyde.

23. The process of claim 22, wherein the phenyldicarbaldehyde is an unsubstituted terephthalaldehyde.

24. The conjugate of claim 10, wherein the phenyldicarbaldehyde is a substituted or unsubstituted terephthalaldehyde.

25. The conjugate of claim 24, wherein the phenyldicarbaldehyde is an unsubstituted terephthalaldehyde.

26. The conjugate of claim 11, wherein the enzyme is a peroxidase.

27. The conjugate of claim 26, wherein the peroxidase is horseradish peroxidase.

28. The conjugate of claim 11, wherein the luminescent substance is a bioluminescent substance, a chemiluminescent substance or a fluorescent substance.

* * * * *